(12) United States Patent
Bruder et al.

(10) Patent No.: US 7,263,157 B2
(45) Date of Patent: Aug. 28, 2007

(54) IMAGING TOMOGRAPHY APPARATUS WITH TWO ACQUISITION SYSTEMS, AND METHOD FOR DETERMINING THEIR SYSTEM ANGLES

(75) Inventors: Herbert Bruder, Höchstadt (DE); Martin Petersilka, Adelsdorf (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 249 days.

(21) Appl. No.: 11/167,024

(22) Filed: Jun. 24, 2005

(65) Prior Publication Data

US 2006/0018423 A1    Jan. 26, 2006

(30) Foreign Application Priority Data

Jun. 24, 2004    (DE)    ................... 10 2004 030 550

(51) Int. Cl.
*G01N 23/083* (2006.01)
(52) U.S. Cl. .............. 378/19; 378/9; 378/15
(58) Field of Classification Search ............ 378/9, 378/15, 19
See application file for complete search history.

(56) References Cited

U.S. PATENT DOCUMENTS

| | | | |
|---|---|---|---|
| 4,384,359 A | 5/1983 | Franke | |
| RE32,961 E * | 6/1989 | Wagner | 378/4 |
| 4,991,190 A | 2/1991 | Mori | |
| 5,469,487 A * | 11/1995 | Hu | 378/9 |
| 6,421,412 B1 | 7/2002 | Hsieh et al. | |
| 6,848,827 B2 * | 2/2005 | Wu et al. | 378/207 |
| 6,873,677 B2 * | 3/2005 | Kaufman | 378/4 |
| 7,130,369 B2 * | 10/2006 | Bruder et al. | 378/9 |
| 2005/0281371 A1 * | 12/2005 | Popescu | 378/19 |

FOREIGN PATENT DOCUMENTS

| | | |
|---|---|---|
| DE | 29 16 848 | 11/1979 |
| DE | 196 15 456 | 10/1997 |

* cited by examiner

*Primary Examiner*—Edward J. Glick
*Assistant Examiner*—Thomas R. Artman
(74) *Attorney, Agent, or Firm*—Schiff Hardin LLP

(57) ABSTRACT

In a tomography apparatus and operating method, at least two acquisition systems are respectively each disposed in the azimuthal direction at respective specific system angles around a common rotation axis. Both system angles can be determined for a substantially constant rotation angle speed of the two acquisition systems on the basis of measurement values, which are calculated at a rotation angle position of a reference object that can be introduced into both measurement planes. The tomography apparatus in this manner enables artifact-free reconstruction of a slice or volume image using the system angles determined in this manner.

17 Claims, 5 Drawing Sheets

IMAGING TOMOGRAPHY APPARATUS WITH TWO ACQUISITION SYSTEMS, AND METHOD FOR DETERMINING THEIR SYSTEM ANGLES

BACKGROUND OF THE INVENTION

1. Field of the Invention

The present invention concerns an imaging tomography apparatus of the type having a first acquisition system with a first radiator and a first detector for generation of detector output signals that are a measure of the absorption of the radiation emanating from the first radiator and passing through a measurement region, and a second acquisition system with a second radiator and a second detector for generation of detector output signals that are a measure for the absorption of the radiation emanating from the second radiator, wherein, in the azimuthal direction, the first acquisition system is disposed at a first system angle and the second acquisition system is disposed at a second system, angle such that they can rotate around a common rotational axis. The invention moreover concerns a method for such a tomography apparatus for determination of the system angle of both acquisition systems.

2. Description of the Prior Art

Other tomography apparatuses with at least two acquisition systems are known from U.S. Pat. No. 4,991,190, German OS 29 51 222, German OS 29 16 848 and U.S. Pat. No. 6,421,412. The advantage of such tomography apparatuses with a number of acquisition systems compared to an apparatus with a single acquisition system is the possibility to examine a subject with an increased sampling speed or with an increased sampling resolution. A high sampling speed is of importance when movement artifacts that are caused by voluntary or involuntary movements of the subject (for example of an organ of an organism to be examined) must be minimized in the reconstructed image. In the examination (for example of a heart), for reconstruction of an artifact-free slice or volume image it is necessary that all exposures used for reconstruction optimally record the same movement state (phase) of the heart at the various rotational angle positions.

In addition to such single image acquisition, entire sequences of slice or volume images are also generated for representation of movement cycles for medical examinations. A higher sampling speed thereby offers the advantage of an improved temporal resolution of the imaged region affected by the movement cycle so that rapidly-changing movement states can be acquired.

A tomography apparatus with a number of acquisition systems can, however, be operated such that a higher sampling resolution is achieved in comparison to a tomography apparatus with only one acquisition system. This is particularly of importance when organs or organ parts of an organism must be resolved in a small examination volume, as in the case of examination of blood vessels, for example.

In a tomography apparatus with a number of acquisition systems, the acquired detector output signals of the various acquisition systems are combined with one another for reconstruction of a slice or volume image, both in the operating mode to increase the sampling speed and in the operating mode to increase the sampling resolution. The combining of the data ensues based on the knowledge of the system angles at which the acquisition systems are arranged in the azimuthal direction around the common rotational axis.

SUMMARY OF THE INVENTION

An object of the present invention is to provide an imaging tomography apparatus and method of the type initially described, wherein system angles of the acquisition systems disposed in the azimuthal direction around a common rotational axis can be determined in a simple manner for various rotation angle speeds.

This object is achieved by an imaging tomography apparatus and method according to the invention, wherein both system angles are determined that are exhibited by a reference object that can be positioned at a reference position within the measurement region but outside of the system axis. From the detector output signals of the first detector, a measurement value is calculated that is associated with the first detector for at least one substantially constant rotation angle speed of both acquisition systems at various rotation angle positions and, from detector output signals of the second detector, a measurement value is calculated that is associated with the second detector for the position of the reference object mapped in the respective detector. The system angles of both acquisition systems are determined from the measurement values thus calculated at the various rotation angle positions. The measurement value associated with the respective detector normally represents the mapped position of the reference object in the detector.

The invention is based on the recognition that the system angles of the two acquisition systems arranged in the azimuthal direction around a common rotational axis can change due to installation tolerances in the manufacturing process and due to strong acceleration forces at high rotational speeds in the operation of the tomography apparatus. The difference between an ideally set desired value of a system angle and the actual system angle of an acquisition system is dependent on the magnitude of the rotational speed. The deviation between the desired value taken into account in the reconstruction of a slice or volume image and the actual existing system angle causes image errors (artifacts) in the reconstructed image, and thus leads to a general worsening of the achievable image quality.

An improvement of the slice or volume images generated from the detector output signals is possible by the inventive determination of system angles, by allowing the exactly-determined system angles to be used for the reconstruction. Artifacts in the slice or volume image due to incorrect underlying system angles of the acquisition systems in the reconstruction are prevented in this manner.

The determination of the system angles is cost-effective and can be particularly simply implemented, because only an evaluation of the detector output signals must be made for a reference object introduced into the measurement region. The system angles of the acquisition systems can be determined with little effort for various rotation angle speeds and thus for any operating mode of the tomography apparatus.

In an embodiment, a particularly efficient and numerically easily convertible determination of the system angles is achieved by the use of a cost function that is a sum of weighted ([addends). Each addend can be formed from the difference of a measurement value associated with the detector and a mapping function, the mapping function describing the connection between a theoretical measurement value of the reference position of the reference object mapped in the detector dependent on the reference position, the geometry of both acquisition systems, the rotation angle position and the system angle to be optimized. The specification of the mapping function preferably ensues in the form of fan geometry coordinates.

A system angle separation (interval) can be determined from the difference of the two system angles. The system angle separation representing only the information about the relative arrangement of the two acquisition systems and that can be directly used in this manner for the reconstruction of an image.

So that the mapping of the reference object on the detectors of both acquisition systems is independent of the rotation angle positions of the acquisition systems and so that a simple evaluation of the detector output signals is possible, the reference object exhibits a rotationally symmetrical design.

The calculation of the measurement value associated with a detector or of the position of the reference object that can be mapped on the detector, is possible in a particularly robust manner without the influence of noise in the detector output signals, when the reference object is imaged on a number of detector elements. The position is advantageously determined from the detector output signals in the sense of an intensity focal point.

The system angles preferably are determined in a calibration process before the actual patient imaging for diagnostic purposes.

In order to also enable immediate access to the determined system angles of the acquisition systems during the normal operation for examination of a patient, in an embodiment of the invention a memory is provided in which the determined system angles can be stored for a number of different, substantially constant rotation angle speeds

DESCRIPTION OF THE PREFERRED EMBODIMENTS

Figure 1:
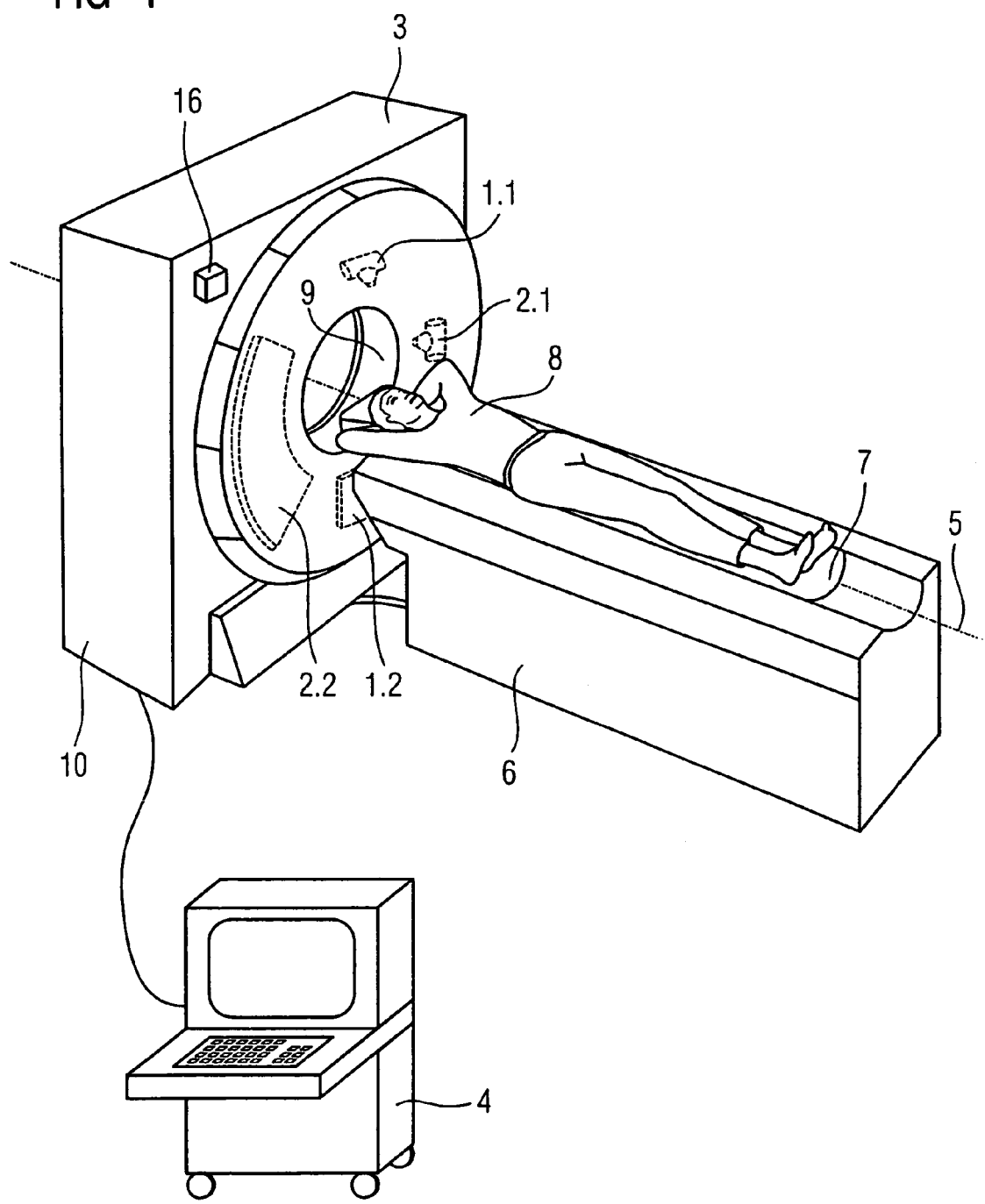
FIG. 1 shows a tomography apparatus according to the invention in a perspective view.

FIG. 1 shows an inventive tomography apparatus 3, here in the form of an x-ray computed tomography apparatus, with a patient bed 6 for acceptance and support of a patient 8. The patient bed 6 has a movable table plate 7 by means of which the patient 8 can be moved through an opening 9 in the housing 10 of the tomography apparatus 3 into the examination or scan region. Moreover, a continuous axial feed of the table plate 7 is effected during a spiral scan.

A gantry (not visible in FIG. 1), that can be rotated with a high speed around a rotation axis 5 running through the patient 8, is located within the tomography apparatus 3.

Two acquisition systems are arranged on the gantry in a predetermined manner to achieve a high scanning speed or a high scan resolution. In the exemplary embodiment, the first acquisition system has an x-ray tube as a first radiator 1.1 and, for example, an eight-row x-ray detector array as a first detector 1.2. In the exemplary embodiment, the second acquisition system has a separate x-ray tube as a second radiator 2.1 and, for example, a separate eight-row x-ray detector array as a second detector 2.2. Both acquisition systems are fixed in their respective positions on the gantry, offset by a specific system angle in the azimuthal direction around the rotation axis 5.

The x-ray detector arrays are, for example, based on an electronically-readable scintillator ceramic, known as a UFC ceramic, and are used for generation of detector output signals that are a measure of the absorption of the radiation emanating from the corresponding radiator 1.1 or 2.1 and passing through the measurement region. However, other detectors, for example wide area detectors with 256 or more rows, can be used for generation of detector output signals.

The detector output signals of both acquisition systems, that preferably scan in the same plane at different rotation angle positions relative to one another, are processed in a control and image computer 4 into a slice or volume image under application of an image reconstruction algorithm. The detector output signals of both acquisition systems are thereby initially merged ("mixed") into a common projection or raw data set. The operation of the tomography apparatus 3 by a physician or technician ensues from the control and image computer 4.

Figure 2:
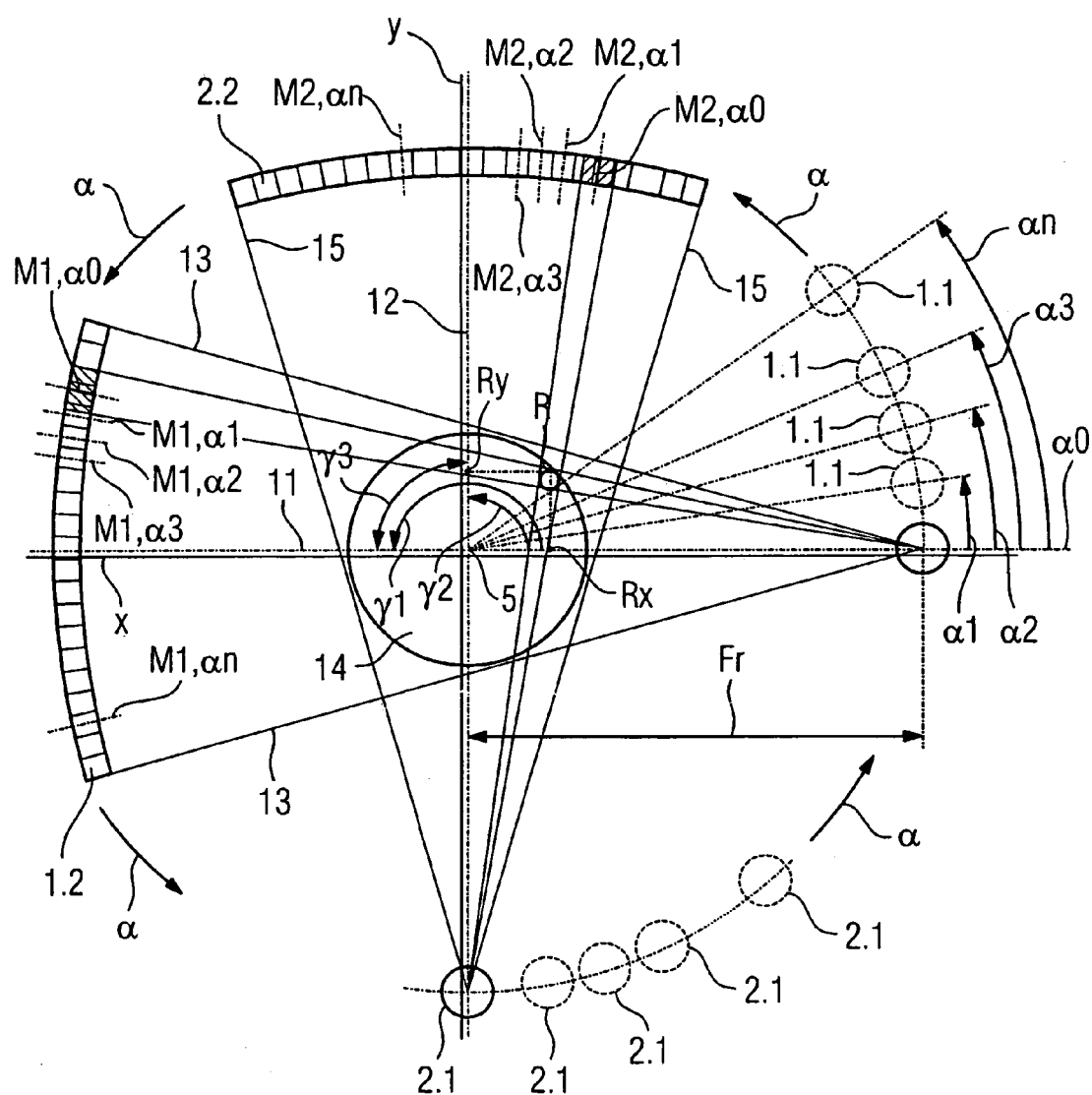
FIG. 2 is in a cross-section of two acquisition systems of the tomography apparatus of FIG. 1 with a reference object positioned in the measurement region of the acquisition system.
Figure 3:
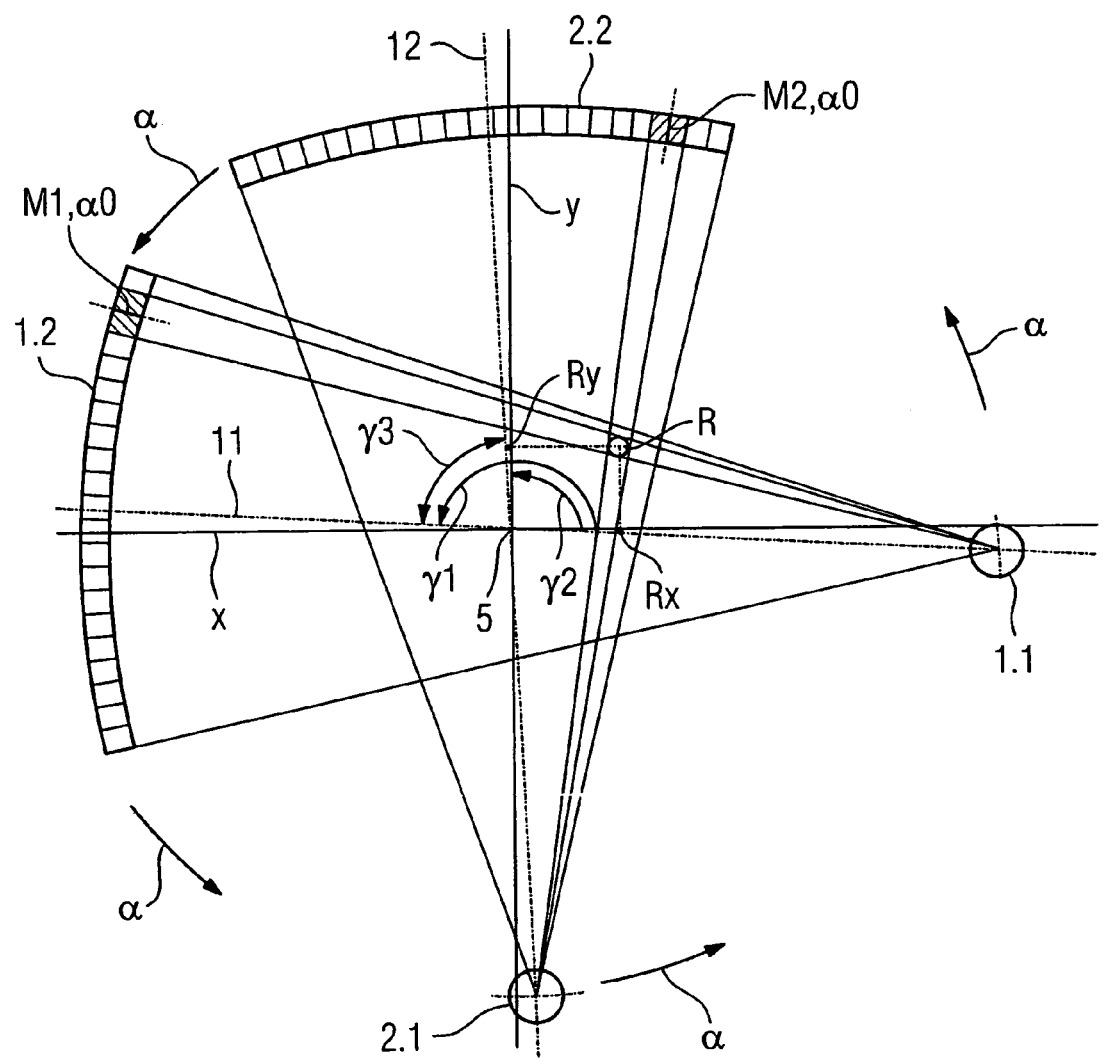
FIG. 3 shows the two acquisition systems of FIG. 2 with shifted system angles.

FIGS. 2 and 3 show both acquisition systems of FIG. 1 in cross-section.

A Cartesian coordinate system with a first axis x and a second axis y and an origin positioned on the rotational axis 5 is used for specification of a system angle associated with the respective acquisition system, for specification of rotation angle positions and for specification of a position of a reference object that can be positioned in a common measurement region 14 of both acquisition systems. All angle and position specifications in the following embodiments refer to the reference system so defined.

Both acquisition systems are mounted such that they can rotate in the azimuthal direction around a common rotation axis 5 in the indicated rotation angle direction $\alpha$. The first acquisition system is mounted at a first system angle $\gamma 1$ and the second acquisition system is mounted at a second system angle $\gamma 2$ around the common rotation axis. The distance of the radiators 1.1, 2.1 and the detectors 1.2, 2.2 from the rotation axis 5 is determined by a focus path radius Fr in the exemplary embodiment. During an examination with the tomography apparatus 3, raw image data that enable a reconstruction of a slice or volume image can be acquired with the two acquisition systems from different projection directions at the various rotation angle positions $\alpha 0, \ldots, \alpha n$ (shown as examples), by rotating the gantry.

As shown in FIG. 2, a reference object R is introduced into the common measurement region 14 at a position Rx, Ry, which generates a projection image in each of the first detector 1.2 and the second detector 2.2, dependent on the rotation angle positions $\alpha 0, \ldots, \alpha n$. The position Rx, Ry of the reference object R can in principle be freely determined; but it must lie outside of the common rotation axis 5 of the two acquisition systems and within the common measurement region. In the cross-section representation, one row of each of the detectors 1.2, 2.2 is shown with a number of detector elements for generation of detector output signals. A first measurement value M1, $\alpha 0$ can be calculated from the detector output signals of the first detector 1.2 generated by the projection image and a corresponding second measurement value M2, $\alpha 0$ can be calculated from the detector output signals of the second detector 2.2. Each measurement value thereby represents the position of the reference object R in the respective detector 1.2 or 2.2.

The measurement values M1, α0, ... M1, αn and M2, α0, ... M2, αn are calculated in this manner in succession from the respective output signals of the detectors 1.2 or and 2.2 at various rotation angle positions α0, ..., αn. The acquisition of the detector output signals ensues for an arbitrary but substantially constant rotation angle speed.

The system angles γ1, γ2 at which the acquisition systems are arranged around the common rotation axis 5 in the azimuthal direction must be known for the reconstruction of a slice or volume image and therefore must exhibit a predetermined value. Due to installation tolerances in the manufacturing process or due to strong acceleration forces during rotation of the gantry, the acquisition systems can be shifted from their original, predetermined position. FIG. 3 shows both acquisition systems from FIG. 2 in the same cross-section representation, with the difference that the originally set system angles of FIG. 1 are shifted, for example, due to installation tolerances. For this reason, different projection images occur in the respective detectors 1.2, 2.2 at the same rotation angle positions α0, ..., αn in comparison with the arrangement of the two acquisition systems shown in FIG. 2. In the reconstruction of a slice or volume image, artifacts would be created in the reconstructed image for this reason without accounting for the exact system angles γ1, γ2.

Figure 4:
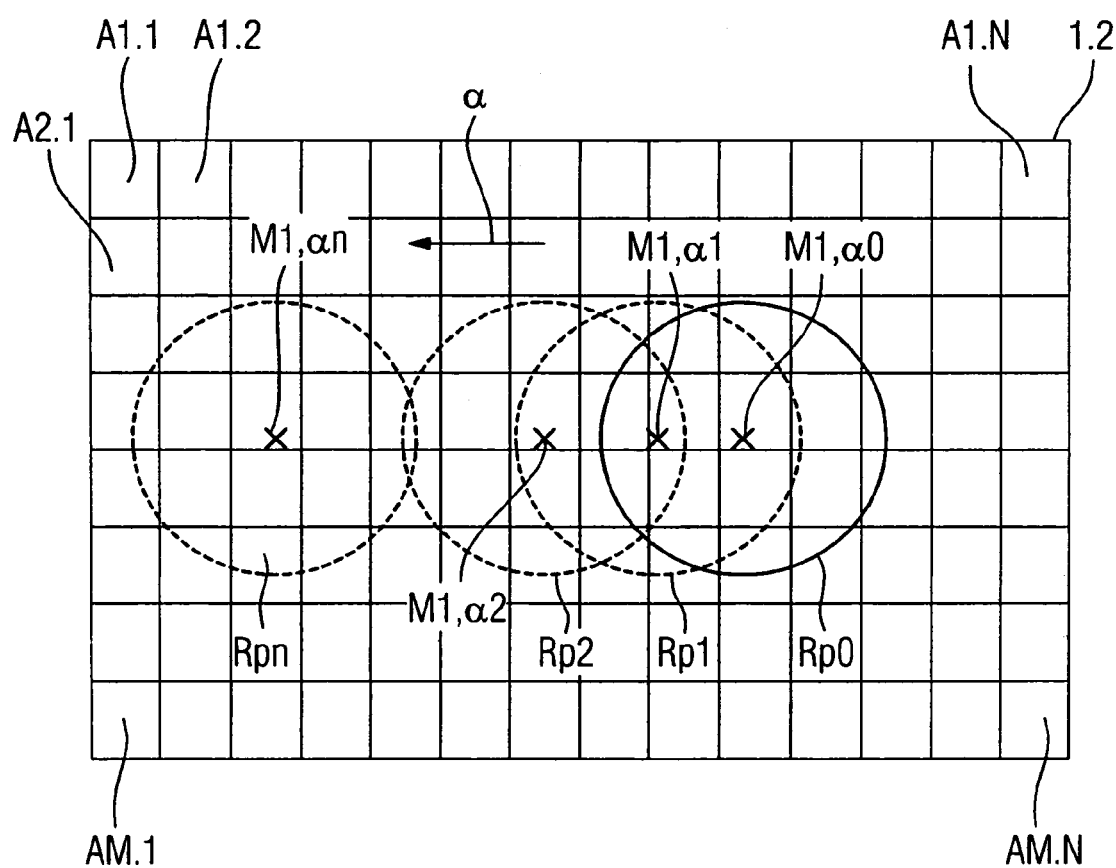
FIG. 4 shows mapping of a reference object on a detector for various rotation angle positions.

FIG. 4 shows the mapping of the reference object R on a detector, here the detector 1.2, as an example for various rotation angle positions α0, ..., αn. A detector array associated with the first detector 1.2 has M rows. N detector elements are present in each row. The detector elements A1.1, ... AM.N are thus arranged in a matrix. A robust calculation (relative to detector noise) of a measurement value M1, α or ... M1, αn can be implemented when the reference object R can be imaged on the multiple detector elements A1.1 through AM.N.

A particularly simple determination of the measurement values M1, α0, ... M1, αn, which can be calculated in a short time on the basis of the detector output signals, can be achieved by the calculation of an intensity focal point. In the simplest case the detector output signals (intensity values) of the detector elements A1.1, ... AM.N are separately weighted according to their position, using row and column coordinates within the detector array, added together and divided by the number of the added values (M×N) for this purpose. Thus, for example, the intensity value "seen" by one detector element is multiplied with the column coordinate of the respective detector element to determine the column coordinate of the intensity focal point. The intensity values weighted in this manner are added together and divided by the number of summands. The value resulting from this procedure represents the column coordinate of the intensity focal point. The row coordinate of the intensity focal point is correspondingly determined.

The calculated measurement value M1, α0 or ... M1, αn corresponds to the position of the reference object R mapped in the detector 1.2 with a precision of sub-pixel units.

In a further embodiment, the reference object R exhibits a rotationally-symmetrical design such that, as shown in FIG. 4, identical mapping profiles Rp0, Rp1, ... Rpn can respectively be generated on the detector 1.2 by mapping for all rotation angle positions α0, ..., αn.

A reference object R that satisfies the just-cited requirements is, for example, an object with spherical or rod-shaped design.

Figure 5:
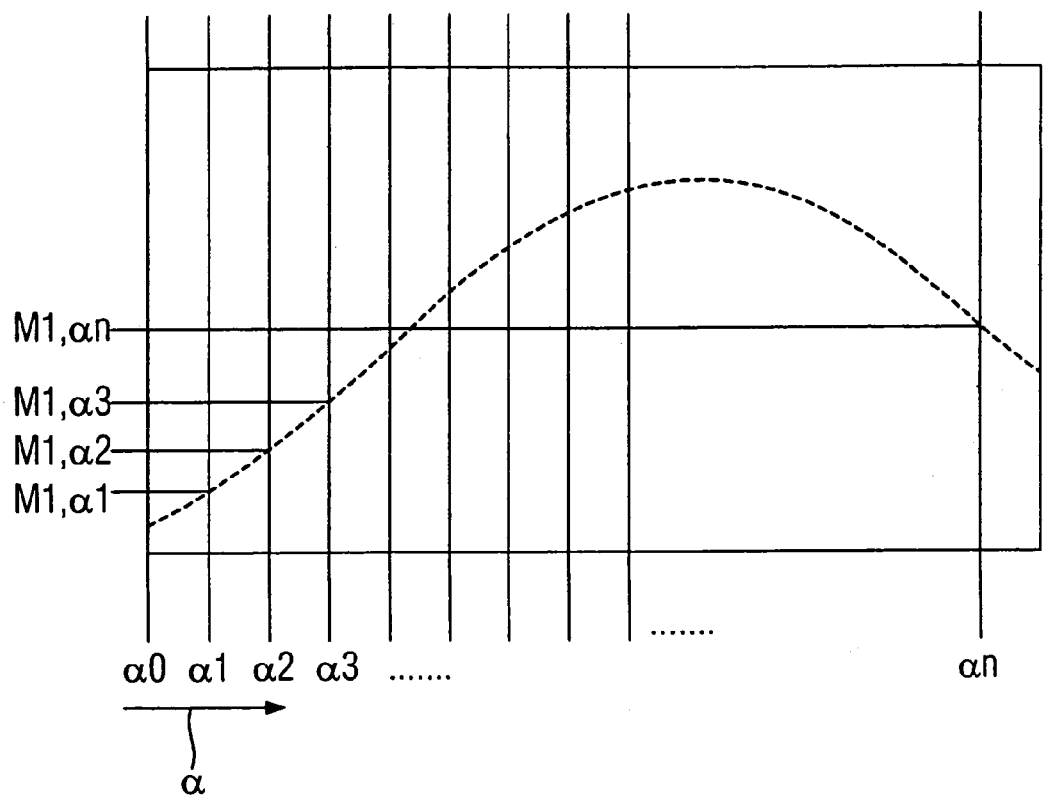
FIG. 5 shows the measurement values of the reference object, associated with the respective detectors, dependent on rotation angle positions of the two acquisition systems.
Figure 5:
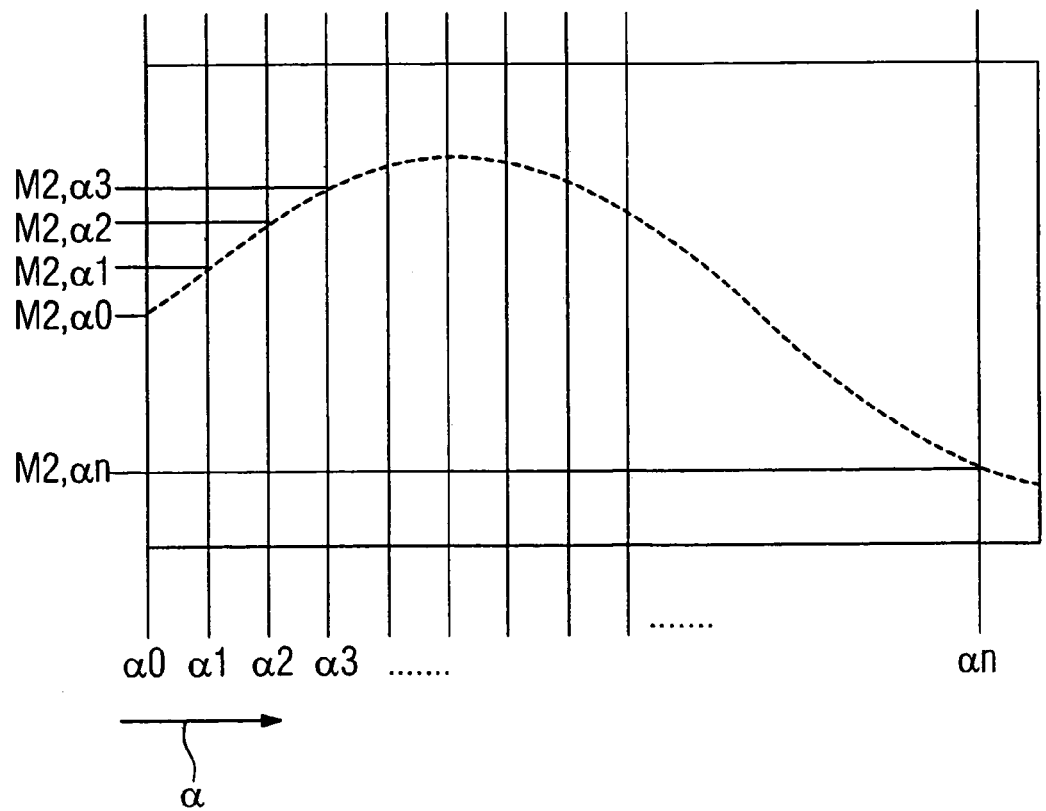

The measurement values M1, α0, ... M1, αn or M2, α0, ... M2, αn associated with the respective detectors 1.2 and 2.2, and calculated during a rotation with constant angular velocity of both acquisition systems at various rotation angle positions α0, ..., αn, serve for determination of the unknown system angles γ1 and γ2. FIG. 5 shows the association between the rotation angle positions of the gantry and the calculated measurement values for the detectors 1.2 or 2.2 in the form of a sinogram.

A particularly efficient and numerically easily convertible determination of the system angles γ1, γ2 is possible by the use of a cost function that is a sum of weighted addends. Each addend can be formed from the difference of a measurement value M1, αi or M2, αi associated with the detector 1.2 or 2.2 and a mapping function S1 or S2.

The mapping function S1 or S2 describes the association between a theoretical measurement value of the reference position of the reference object R mapped in the detector 1.2 or 2.2 dependent on the reference position Rx, Ry of the reference object R, the focal path radius Fr, the rotation angle position αi and the system angle γ1 or γ2 to be optimized.

The mapping function S1 or S2 typically can be specified in the form of fan geometry coordinates and has the following form:

$$S_{1/2}(\alpha_i, R_x, R_y, \gamma_{1/2})_{i=1,\ldots,n} = \arctan\left(\frac{-R_x \cdot \sin(\gamma_{1/2} + \alpha_i) + R_y \cdot \cos(\gamma_{1/2} + \alpha_i)}{F_r + R_x \cdot \cos(\gamma_{1/2} + \alpha_i) + R_y \cdot \sin(\gamma_{1/2} + \alpha_i)}\right)$$

Based on the mapping function S1 or S2, a cost function Fa can be formed and minimized or optimized such that both the unknown position Rx, Ry of the reference object R and the system angles γ1, γ2 can be determined. The determination of the system angles γ1, γ2 can be realized separate from one another or uniformly, depending on the design of the cost function. A cost function to determine the position Rx, Ry of the reference object R and to determine the system angle γ1, γ2 can be specified according to the following, whereby the addends are formed from the difference of the cited mapping function S1 or, respectively, S2 and the measurement values M1, α0, ... M1, αn or M2, α0, ... M2, αn calculated at various rotation angle positions:

$$F_a(R_x, R_y, \gamma_{1/2}) = \sum_{i=0}^{n} (S_{1/2}(\alpha_i, R_x, R_y, \gamma_{1/2}) - M_{1/2}, \alpha_i)^2 \quad (2)$$

The determination of the position Rx, Ry of the reference object R and of the system angle γ1, γ2 can, however, also be uniformly converted into a simpler form as a cost function:

$$F_b(R_x, R_y, \gamma_1, \gamma_2) = \quad (3)$$
$$\sum_{i=0}^{n} (S_1(\alpha_i, R_x, R_y, \gamma_1) - M_1, \alpha_i)^2 + (S_2(\alpha_i, R_x, R_y, \gamma_2) - M_2, \alpha_i)^2$$

The difference values considered in the cost function Fa or Fb are quadratically weighted, but other weightings or cost functions are also possible with which the minimization can be implemented for determination of the system angles. The optimization of the cost function Fa or Fb can be achieved by standard methods that are known from the literature. Among such standard methods are, for example, the simplex method by Nelder and Mead ("Optimization and Approximation", Peter Kosmol, Gruyter 1991), Powell's algorithm or optimization with a generic algorithm.

Based on the system angles $\gamma 1$, $\gamma 2$ that are determined, a system angle interval $\gamma 3=\gamma 1-\gamma 2$ is formed that advantageously represents only the information about the relative arrangement of the two acquisition systems. The system angle interval $\gamma 3$ that is determined can be used in the reconstruction of a slice or volume image in which the exact rotation angle positions of the individual projection images of the acquisition systems are used in the conversion into parallel geometry with azimuthal rebinning. An interpolation of the projection data from the detectors 1.2, 2.2 at equidistant rotation angle positions is necessary in a reconstruction into fan geometry coordinates.

The system angles $\gamma 1$, $\gamma 2$ of both acquisition systems can be inventively determined for various, substantially constant rotation angle speeds. The storage of the system angles $\gamma 1$, $\gamma 2$ for a number of rotation angle speeds in a memory 16 associated with the tomography apparatus 3 enables immediate access to the determined system angles $\gamma 1$, $\gamma 2$, even during an examination in which the gantry is operated with various rotation angle speeds.

Although modifications and changes may be suggested by those skilled in the art, it is the intention of the inventors to embody within the patent warranted hereon all changes and modifications as reasonably and properly come within the scope of their contribution to the art.

We claim:

1. An imaging tomography apparatus comprising:
   a first data acquisition system disposed at a first system angle in an azimuthal direction, comprising a first radiation radiator that emits radiation passing through a measurement region and a first radiation detector that generates first detector output signals representing absorption of said radiation emitted by said first radiation radiator;
   a second data acquisition system disposed at a second system angle in said azimuthal direction, different from said first system angle, comprising a second radiation radiator that emits radiation passing through said measurement region and a second radiation detector that generates second detector output signals representing absorption of said radiation emitted by said second radiation radiator;
   said first data acquisition system and said second data acquisition system being mounted for rotation around a rotational axis common to both said first data acquisition system and said second data acquisition system;
   a reference object positionable at a reference position in said measurement region but outside of said rotational axis; and
   a calculation unit, supplied with said first detector output signals and said second detector output signals, that calculates, for each of a plurality of rotation angle positions of said first and second data acquisition systems with said first and second data acquisition systems being rotated at a substantially constant rotation angle speed, a first measurement value from said first detector output signals representing attenuation by said reference object of said radiation emanating from said first radiation radiator, and a second measurement value from said second detector output signals representing attenuation by said reference object of said radiation emanating from said second radiation radiator, and that determines the first and second system angles from said first and second measurement values for each of said plurality of rotation angle positions.

2. An imaging tomography apparatus as claimed in claim 1 wherein said calculation unit calculates a first mapping function describing, in fan geometry coordinates, an association between a theoretical first measurement value of said reference position, mapped on said first detector, and said first system angle, and calculates a second mapping function, describing, in fan geometry coordinates, an association between a theoretical second measurement value of said reference position, mapped on said second radiation detector, and said second system angle, and calculates a first cost function comprising a sum of weighted differences of said first measurement values and said first mapping function, and calculates a second cost function comprising a sum of weighted differences of said second measurement values and said second mapping function, and wherein said calculation unit determines said first system angle by optimizing said first cost function and determines said second system angle by optimizing said second cost function.

3. An imaging tomography apparatus as claimed in claim 2 wherein said first data acquisition system has a geometry associated therewith and wherein said second data acquisition system has a geometry associated therewith, and wherein said calculation unit forms said first mapping function dependent on said reference position, the geometry of said first data acquisition system, the rotation angle position, and said first system angle, and forms said second mapping function dependent on said reference position, the geometry of said second data acquisition system, the rotation angle position, and said second system angle.

4. An imaging tomography apparatus as claimed in claim 1 wherein said calculation unit determines a system angle interval for each of said plurality of rotation angle positions as a difference between said first system angle and said second system angle.

5. An imaging tomography apparatus as claimed in claim 4 wherein said first and second data acquisition systems are adapted to interact with an examination subject to respectively obtain first and second image data sets from said examination subject, after said position correction values have been obtained, and wherein said imaging tomography apparatus comprises an image reconstruction computer, supplied with said first and second image data sets and the system angle intervals, that reconstructs an image of the examination subject with the respective first and second image data sets and with the system angle intervals.

6. An imaging tomography apparatus as claimed in claim 1 wherein said reference object has a rotationally symmetrical shape.

7. An imaging tomography apparatus as claimed in claim 1 wherein said first radiation detector comprises multiple first detector elements and wherein said second radiation detector comprises multiple second detector elements, and wherein said reference object has a size so as to attenuate radiation on a number of said first detector elements and on a number of said second detector elements.

8. An imaging tomography apparatus as claimed in claim 1 wherein said calculation unit calculates said first measurement value as a first intensity focal point for said first radiation detector and calculates said second measurement value as a second intensity focal point for said second radiation detector.

9. An imaging tomography apparatus as claimed in claim 1 wherein said calculation unit calculates said first and second system angles for each of a number of substantially constant rotation angle speeds of said first and second data acquisition systems, and wherein said imaging tomography apparatus comprises a memory connected to said calculation unit for storing the respective first and second system angles position correction values with a designation of the rotation angle speed for which the respective first and second system angles were obtained.

10. A method for operating an imaging tomography apparatus comprising a first data acquisition system disposed at a first system angle in an azimuthal direction, comprising a first radiation radiator that emits radiation passing through a measurement region and a first radiation detector that generates first detector output signals representing absorption of said radiation emitted by said first radiation radiator, and a second data acquisition system disposed at a second system angle in said azimuthal direction, different from said first system angle, comprising a second radiation radiator that emits radiation passing through said measurement region and a second radiation detector that generates second detector output signals representing absorption of said radiation emitted by said second radiation radiator; said first data acquisition system and said second data acquisition system being mounted for rotation around a rotational axis common to both said first data acquisition system and said second data acquisition system, said method comprising the steps of:

positioning a reference object at a reference position in said measurement region;

electronically calculating, for each of a plurality of rotation angle positions of said first and second data acquisition systems with said first and second data acquisition systems being rotated at a substantially constant rotation angle speed, a first measurement value from said first detector output signals representing attenuation by said reference object of said radiation emanating from said first radiation radiator, and a second measurement value from said second detector output signals representing attenuation by said reference object of said radiation emanating from said second radiation radiator;

electronically determining first and second system angles from said first and second measurement values for each of said plurality of rotation angle positions; and dependent on said first and second system angles irradiating an examination subject and obtaining image data of the subject with said first and second data acquistion systems, and reconstructing an image of the subject from said image data.

11. A method as claimed in claim 10 comprising electronically calculating a first mapping function describing, in fan geometry coordinates, an association between a theoretical first measurement value of said reference position, mapped on said first detector, and said first system angle, and electronically calculating a second mapping function, describing, in fan geometry coordinates, a connection between a theoretical second measurement value of said reference position, mapped on said second radiation detector, and said second system angle, and electronically calculating a first cost function comprising a sum of weighted differences of said first measurement values and said first mapping function, and electronically calculating a second cost function comprising a sum of weighted differences of said second measurement values and said second mapping function, and wherein said electronically determining said first system angle by optimizing said first cost function and electronically determining said second system angle by optimizing said second cost function.

12. A method as claimed in claim 11 wherein said first data acquisition system has a geometry associated therewith and wherein said second data acquisition system has a geometry associated therewith, and comprising forming said first mapping function dependent on said reference position, the geometry of said first data acquisition system, the rotation angle position, and said first system angle, and forming said second mapping function dependent on said reference position, the geometry of said second data acquisition system, the rotation angle position, and said second system angle.

13. A method as claimed in claim 10 comprising electronically determining a system angle interval for each of said plurality of rotation angle positions as a difference between said first system angle and said second system angle.

14. A method as claimed in claim 13 wherein the step of irradiating an examination subject comprises irradiating an examination subject with said first and second data acquisition systems to respectively obtain first and second image data sets from said examination subject, after said system angle intervals have been determined, and electronically reconstructing an image of the examination subject with the respective first and second image data sets corrected and with the system angle intervals.

15. A method as claimed in claim 10 comprising employing an object as said reference object having a rotationally symmetrical shape.

16. A method as claimed in claim 10 comprising electronically calculating said first measurement value as a first intensity focal point for said first radiation detector and electronically calculating said second measurement value as a second intensity focal point for said second radiation detector.

17. A method as claimed in claim 10 comprising electronically calculating said first and second system angles for each of a number of substantially constant rotation angle speeds of said first and second data acquisition systems, and electronically storing the respective first and second system angles with a designation of the rotation angle speed for which the respective first and second system angles.

* * * * *